US009962293B2

(12) United States Patent
Easter (10) Patent No.: US 9,962,293 B2
(45) Date of Patent: May 8, 2018

(54) OPTICAL MICROPHONE FOR IMPLANTABLE HEARING INSTRUMENT (71) Applicant: Cochlear Limited, Macquarie University, NSW (AU)

(72) Inventor: James R. Easter, Lyons, CO (US)

(73) Assignee: Cochlear Limited, Macquarie University, NSW (AU)

( * ) Notice: Subject to any disclaimer, the term of this patent is extended or adjusted under 35 U.S.C. 154(b) by 272 days.

(21) Appl. No.: 14/868,862

(22) Filed: Sep. 29, 2015

(65) Prior Publication Data
US 2016/0015567 A1 Jan. 21, 2016

Related U.S. Application Data (62) Division of application No. 13/550,958, filed on Jul. 17, 2012, now Pat. No. 9,155,660.

(60) Provisional application No. 61/510,201, filed on Jul. 21, 2011.

(51) Int. Cl.
A61F 11/04 (2006.01)
H04R 25/00 (2006.01)
H04R 23/00 (2006.01)
A61N 1/36 (2006.01)

(52) U.S. Cl.
CPC ........ A61F 11/045 (2013.01); A61N 1/36032 (2013.01); H04R 23/008 (2013.01); H04R 25/604 (2013.01); H04R 2225/67 (2013.01)

(58) Field of Classification Search
CPC ... A61F 11/045; H04R 25/604; H04R 23/008; H04R 2225/67; A61N 1/36032
USPC .................................. 398/132–134
See application file for complete search history.

(56) References Cited

U.S. PATENT DOCUMENTS

| 4,479,265 | A | 10/1984 | Muscatell | |
| 6,014,239 | A * | 1/2000 | Veligdan | H04B 10/114 381/170 |
| 8,014,871 | B2 | 9/2011 | Dalton | |
| 9,155,660 | B2 * | 10/2015 | Easter | A61F 11/045 |
| 2009/0109423 | A1 | 4/2009 | Carr | |
| 2011/0029041 | A1 | 2/2011 | Wiskerke | |
| 2013/0096367 | A1 | 4/2013 | Easter | |

* cited by examiner

Primary Examiner — Leslie C Pascal
(74) Attorney, Agent, or Firm — Martin J. Cosenza; Pilloff & Passino LLP (57) ABSTRACT An implanted microphone is provided that allows for isolating an acoustic response of the microphone from vibration induced acceleration responses of the microphone. The present invention measures the relative motion between a microphone diaphragm, which is responsive to pressure variations in overlying media caused by acoustic forces and acceleration forces, and a cancellation element that is compliantly mounted within a housing of the microphone, which moves primarily in response to acceleration forces. When the microphone and cancellation element move substantially in unison to acceleration forces, relative movement between these elements corresponds to the acoustic response of the microphone diaphragm. This relative movement may be directly measured using various optical measuring systems.

27 Claims, 9 Drawing Sheets

OPTICAL MICROPHONE FOR IMPLANTABLE HEARING INSTRUMENT

CROSS REFERENCE

The present application is a Divisional of and claims priority to U.S. patent application Ser. No. 13/550,958, filed Jul. 17, 2012, naming James R. Easter as an inventor, which claims priority to U.S. Provisional Patent Application No. 61/510,201, filed Jul. 21, 2011. This application claims priority to each of these applications, and the disclosures of each of these applications are hereby incorporated by reference herein in their entirety.

FIELD

The present disclosure relates to implanted microphone assemblies, e.g. as employed in hearing aid instruments, and more particularly, to implanted microphone assemblies having improved acoustic sensitivity and reduced sensitivity to non-acoustic vibration.

BACKGROUND OF THE INVENTION

Until recently, a large number of people affected by sensorineural hearing loss of 55 dB or more have been unable to receive adequate therapeutic benefit from any available technology. This problem has been alleviated to some extent by the development of a class of hearing aids generally referred to as implantable hearing instruments, which include, for example, middle ear implants and cochlear implants. Generally, such implantable hearing instruments utilize an implanted transducer to stimulate a component of the patient's auditory system (e.g., tympanic membrane, ossicles and/or cochlea). By way of example, one type of implantable transducer includes an electromechanical transducer having a magnetic coil that drives a vibratory actuator. The actuator is positioned to interface with and stimulate the ossicular chain of the patient via physical engagement. (See e.g. U.S. Pat. No. 5,702,342). In this regard, one or more bones of the ossicular chain are made to mechanically vibrate causing stimulation of the cochlea through its natural input, the so-called oval window.

Amongst users of implantable hearing instruments, there is a strong desire for a small, fully implantable system. In such hearing instruments, the entirety of the instruments of various hearing augmentation components, including a microphone assembly, is positioned subcutaneously on or within a patient's skull, typically at locations proximate the mastoid process.

As may be appreciated, implantable hearing instruments that make use of an implanted microphone require that the microphone be positioned at a location that facilitates the receipt of acoustic signals. For such purposes, such implantable microphones may be typically positioned in a surgical procedure between a patient's skull and skin, at a location rearward and upward of a patient's ear (e.g., in the mastoid region). Accordingly, the hearing instrument must overcome the difficulty of detecting external sounds (i.e., acoustic vibrations) after attenuation by a layer of skin. In this regard, a subcutaneously located microphone must provide adequate acoustic sensitivity while being covered by a layer of skin between about 3 mm and 12 mm thick.

Further, a subcutaneously located microphone must also be able to discriminate between acoustic sounds and unwanted vibrations. That is, acceleration within patient tissue (e.g., caused by tissue-borne vibration) may cause pressure fluctuations that are commingled with pressure fluctuations caused by acoustic sounds impinging on tissue overlying an implanted microphone. This undesirable commingling of ambient acoustic signals and tissue-borne acceleration signals is at the root of several problems facing the designers of implantable hearing systems.

One particular problem relates to vibrations caused by the implant wearer's voice, chewing or vibration caused by the hearing instrument itself (e.g., an electro-mechanical transducer) that may generate distortion of a wearer's own voice, provide feedback and/or reduce acoustic sensitivity. For example, sound emanating from the vocal chords of a person wearing an implantable hearing instrument passes through the bony structure of the head (i.e., as a vibration) and reaches the implanted microphone of the implantable middle ear hearing system or fully implantable cochlear implant. The vibration reaches the microphone and may induce pressure fluctuations within the skin due to acceleration. Accordingly, such pressure fluctuations may be amplified just as a pressure fluctuation caused by the deflection of the skin's surface by an acoustic sound. In this regard, the implanted microphone detects the combination of these two sources as a single varying pressure. Further, in systems employing a middle ear stimulation transducer, the microphone may produce feedback by picking up and amplifying vibration caused by the stimulation transducer. As such, the bone-borne vibration undesirably limits the maximum achievable gain of the implantable hearing instrument.

In order to achieve a nearly natural quality of the implant wearer's voice and detect acoustic signals with sufficient sensitivity, an implanted microphone needs to isolate acoustic responses from non-acoustic vibration responses. The aim of the present invention is to design an implantable microphone that achieves these goals.

SUMMARY OF THE INVENTION

Although all microphones possess some degree of acceleration sensitivity, unwanted responses from acceleration is not significantly limiting to the performance of acoustic microphones, that is, microphones designed to operate in air. The inventor of the present invention has recognized that the same is not true, however, for subdermal/implanted microphones as acceleration within tissue arising from tissue-borne vibration (e.g., from talking or chewing) causes pressure fluctuations that are combined/commingled by the implanted microphone with pressure fluctuations caused by external/ambient sounds. In this regard, pressure fluctuations in tissue (e.g., overlying an implanted microphone) may arise from external pressures such as ambient acoustic signals (i.e., sound) impinging on the skin as well as from acceleration within the tissue caused by vibration. Accordingly, a method and system for distinguishing or isolating an acoustic signal component from a commingled signal is desirable.

The present inventor has recognized that previous attempts to isolate an acoustic signal from a combined acoustic and acceleration output response of an implanted microphone have typically focused on separately measuring acceleration forces applied to an implanted microphone and subsequently removing a signal indicative of those acceleration forces from a signal indicative of the combined output response. The inventor has further recognized that, rather than measuring a combined acoustic and acceleration output response of an implanted microphone, it is possible to isolate and more directly measure the acoustic response. That is, rather than monitoring a combined output response, the present invention allows for measuring an acoustic response of an implanted microphone even in the presence of acceleration forces acting on the microphone. Such measurement may significantly reduce or eliminate the need for subsequent processing to remove undesired signals from the microphone response. Accordingly, improved gain and hearing augmentation may be achieved.

The inventor has recognized that microphone acoustic response isolation may be achieved by monitoring the relative movement of the microphone diaphragm, which is subject to acoustic and acceleration forces, relative to a compliant cancellation element that moves in response to acceleration forces but has little or no response to acoustic forces. That is, when the microphone diaphragm and cancellation element have substantially common movement in relation to commonly applied acceleration forces, the relative movement between these elements is primarily due to the difference in the total forces applied to these elements. Specifically, this difference in forces is primarily due to the acoustic forces applied to the microphone diaphragm. Accordingly, by monitoring relative movement between the diaphragm and the cancellation element it is possible to isolate the acoustic response of the microphone diaphragm from a combined response of the microphone diaphragm including response to acoustic and acceleration forces.

The inventor has further determined that such relative movement may be effectively monitored or measured optically. That is, relative movement may be monitored by optically measuring a path length between an inside surface of an implantable microphone housing (e.g., inside surface of the diaphragm) and a cancellation element that is operative to move in relation to acceleration forces. Changes to the path length may substantially correlate to the acoustic forces applied to the microphone diaphragm. In order to measure the optical path length between the inside surface of the microphone housing and the cancellation element, a light source is provided that is operative to project a beam between these two elements where this beam is subsequently received by an optical detector. This optical detector generates an output signal that is indicative of the relative movement between these elements. Accordingly, such an output may be used to generate a stimulation or drive signal for actuating an actuator or other stimulation element of an implantable hearing instrument such as, without limitation, a middle ear transducer, a cochlear electrode and/or a bone anchored vibrating element. In one arrangement, generating a stimulation signal may include additional processing of the output to provide, for example, frequency shaping, amplification, compression, noise reduction/cancellation or other signal conditioning, including conditioning based on patient-specific fitting parameters.

According to a first aspect, an implantable microphone is provided. The microphone includes a housing that has an internal chamber and a flexible housing portion that is operative to move in response to pressure variations present in media overlying the flexible housing portion. Such pressure variations may include acoustic forces, acceleration forces (e.g., tissue-borne vibrations) and/or a combination of these forces. The microphone also includes a cancellation element that is disposed within the internal chamber of the housing. At least a portion of this cancellation element is operative to move relative to the housing in response to acceleration forces that act on the housing. A light source disposed within the housing generates an output beam. At least a portion of the output beam is received by an optical detector after this portion of the output beam has traveled an optical path between the light source and optical detector that includes at least one reflection off of the flexible housing portion and at least one reflection off of the cancellation element. The optical detector generates an output signal that is indicative of the received light.

It will be appreciated that the movement of the flexible housing portion, which in various arrangements may be formed of a microphone diaphragm extending over an aperture in the housing, relative to the cancellation element changes the path length between these elements and thus alters the light beam as received by the detector. For instance, in one arrangement, the change in the light path modulates the light beam such that when an output of the optical detector is demodulated (e.g., using an un-modulated beam) the demodulated signal generates an output indicative of the movement of the flexible housing portion relative to the cancellation element. In another arrangement, the change in the path length may alter the size (e.g., diameter or other cross-dimension) of the output beam as received by the optical detector. In this latter regard, an increase or decrease of the path length between the source and optical detector may change the cross-dimension of, for example, a converging light beam as received at the optical detector. Accordingly, such a change in the diameter or cross dimension alters the output of the optical detector and is indicative of the relative movement of the diaphragm relative to the cancellation element. In any arrangement, the relative movement is indicative of the acoustic response of the flexible housing portion with reduced response to acceleration forces.

The output of the optical detector may be utilized to generate a drive signal for receipt by an auditory stimulation device. In this regard, the output signal may be processed by a processor that is located within the microphone housing. Alternatively, the output signal may be provided to a separate housing that includes processing equipment. In either arrangement, additional processing may be performed to provide, for example, frequency shaping, amplification, compression, noise reduction or other signal conditioning, including conditioning based on patient-specific fitting parameters.

In one arrangement, the light source is formed of a laser such as a laser diode or converging laser. In a particular embodiment, the laser source forms part of a Laser Doppler Velocimeter (LDV). In this arrangement, an output of the laser is separated into two or more identical beams. One of these beams, a reference beam is provided to the optical detector free of reflection off of the flexible housing portion and/or the cancellation element. In contrast, the other beam, a test beam, reflects off of one or both of the vibrating elements in order to modulate the beam. The LDV may include one or more beam splitters for splitting and/or combining beams as well as one or more frequency shifting elements such as, and without limitation, a Bragg cell.

In another arrangement, a convergent/converging laser is utilized to identify path length changes between the flexible housing portion and the cancellation element. At rest (e.g., during static conditions), the laser generates a footprint on the photo diode having a fixed cross-dimension. During movement, this cross-dimension changes and generates an output signal that is indicative of the relative movement between the elements.

In all cases, it may be desirable that the magnitude of the response of the cancellation element to acceleration be chosen to substantially match the response of the flexible housing portion to acceleration. Likewise, it may be desirable that the phases of these elements substantially match to achieve enhanced cancellation. Stated otherwise, it may be preferred that such magnitude and phase matching occur in a frequency range of interest (e.g., frequencies important to hearing). This may require that the resonant frequency of each the flexible housing portion and cancellation element be less than about 2000 Hz and more preferably less than about 200 Hz. These resonant frequencies are typically below an acoustic hearing frequency range. Further, it may be desirable that the flexible housing portion and cancellation element have substantially equal resonant frequencies and/or equal damping factors.

The cancellation element may be any compliant structure that is operative to move in response to acceleration forces applied to the microphone. For instance, the cancellation element may include a compliantly supported mass (e.g., a proof or seismic mass). Inertial movement of the proof mass in response to acceleration forces may physically match movement of the flexible housing portion in response to acceleration. Any appropriate means may be utilized to compliantly mount and/or damp the movement of the cancellation element including, without limitation, mechanical springs, fluid bladders/cushions and/or magnets.

According to another aspect, a method is provided for isolating an acoustic response from a combined response of an implanted microphone. The method includes reflecting a first light beam off an inside surface of a housing of the implantable hearing instrument and/or reflecting that light beam off a cancellation element within an internal chamber of the housing. The method further includes receiving the first light beam at an optical detector after a reflection off of one or both of the inside surface of the housing and cancellation element and generating an output signal indicative of relative movement between these elements.

The method may further include processing the output signal to generate a vibration signature of the inside surface of the housing. This vibration signature may be indicative of a movement of the inside surface of the housing relative to the cancellation element caused by the acoustic forces applied to that surface. The method may further include generating a stimulation signal utilizing the vibration signature where the stimulation signal is subsequently operative for use with an actuator/stimulator of an implantable hearing instrument.

DETAILED DESCRIPTION OF THE INVENTION

Figure 1:
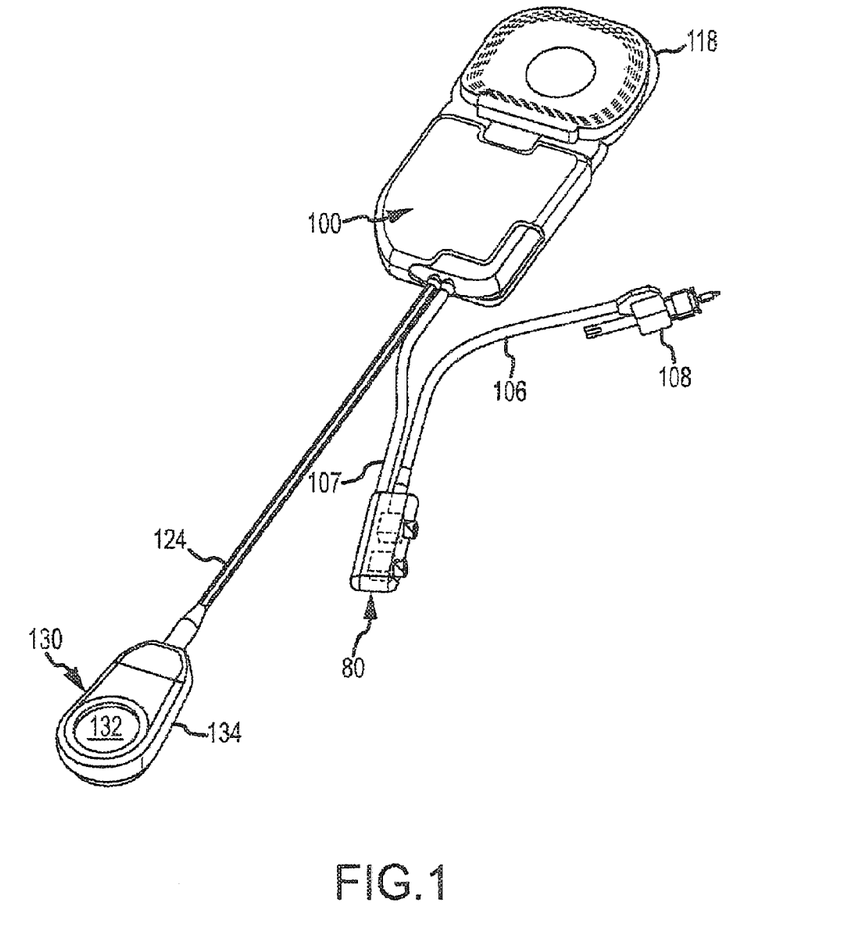
FIG. 1 illustrates a fully implantable hearing instrument.
Figure 2:
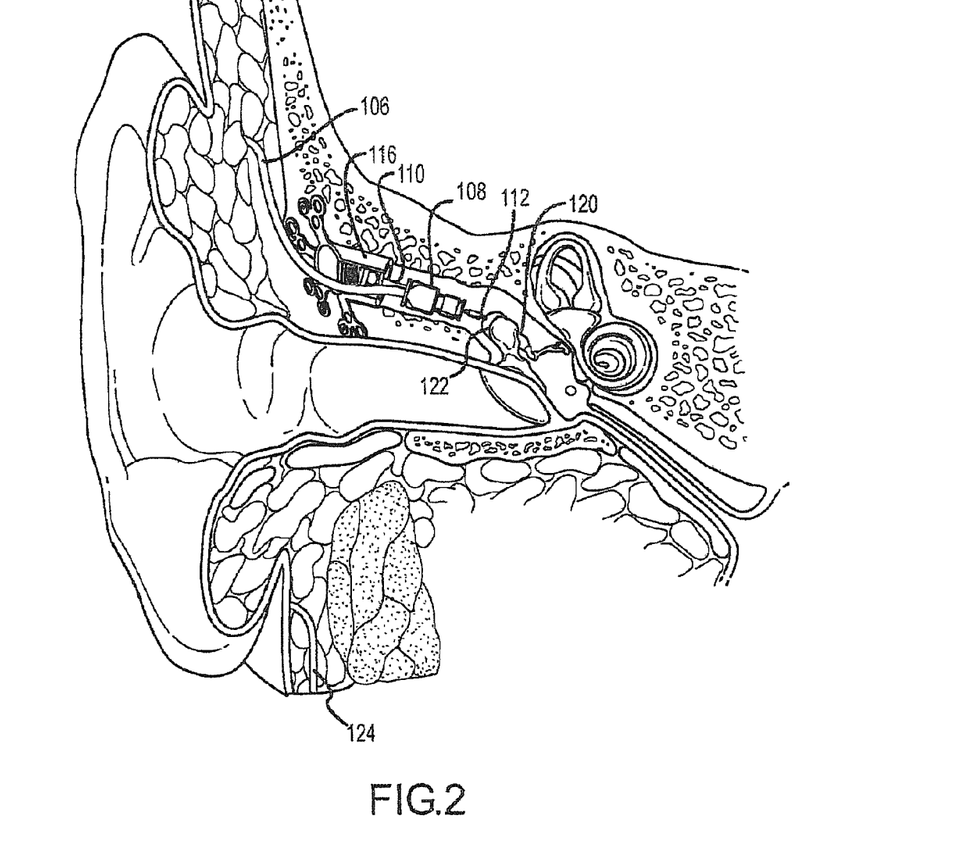
FIG. 2 illustrates the hearing instrument of FIG. 1 as implanted.
Figure 3:
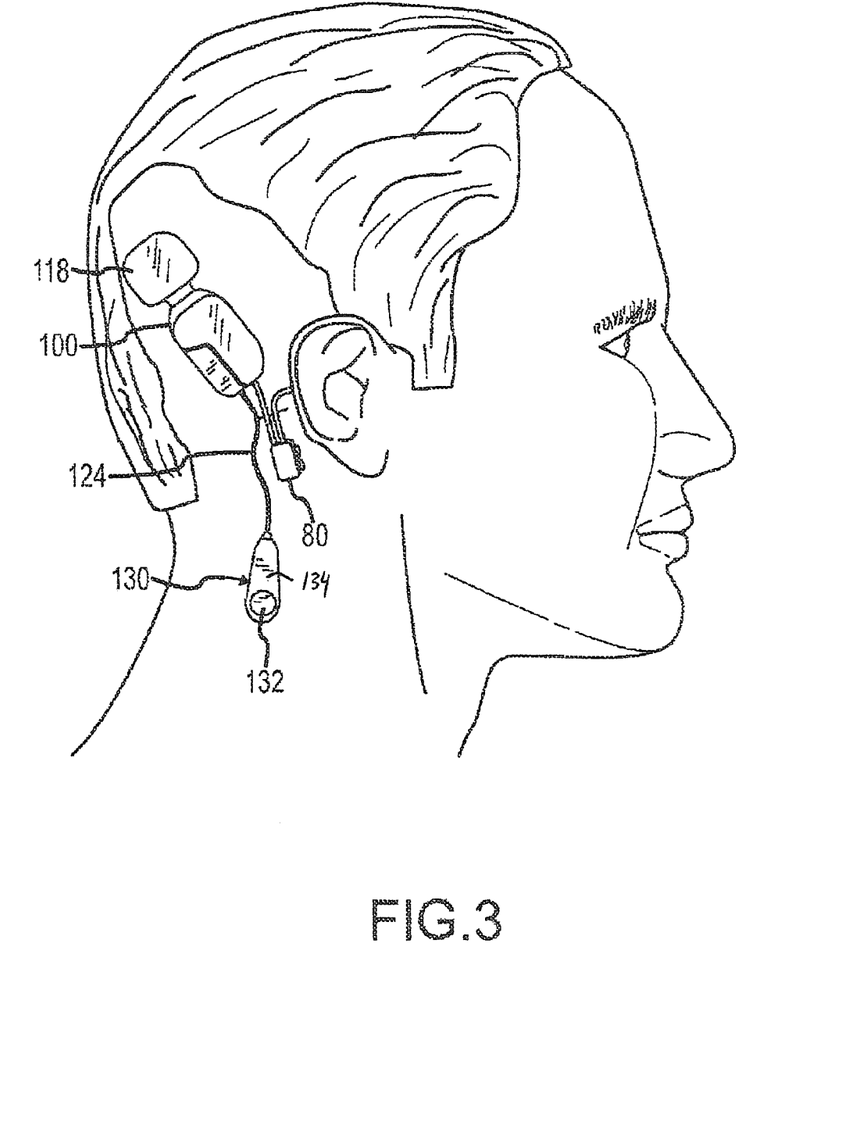
FIG. 3 illustrates the implantable hearing instrument of FIG. 1 as positioned on a wearer.

Reference will now be made to the accompanying drawings, which at least assist in illustrating the various pertinent features of the presented inventions. In this regard, the following description of a hearing instrument is presented for purposes of illustration and description. Furthermore, the description is not intended to limit the inventions to the forms disclosed herein. Consequently, variations and modifications commensurate with the following teachings, and skill and knowledge of the relevant art, are within the scope of the presented inventions. The embodiments described herein are further intended to explain the best modes known of practicing the inventions and to enable others skilled in the art to utilize the inventions in such, or other embodiments and with various modifications required by the particular application(s) or use(s) of the presented inventions.
Hearing Instrument System:

FIGS. 1-3 illustrate one embodiment of a system in which various aspects of the disclosed inventions may be incorporated. The illustrated embodiment is a fully implantable hearing instrument system that provides mechanical stimulation to the middle ear of a patient. As will be appreciated, certain aspects of the presented inventions may be employed in conjunction with different implantable systems including but not limited to semi-implantable hearing instruments, bone conduction hearing instruments, as well as inner ear hearing instruments (e.g., cochlear implants), and therefore, the illustrated application is for purposes of illustration and not by way of limitation.

In the illustrated system, a biocompatible implant housing 100 is located subcutaneously on a patient's skull. The implant housing 100 includes an implanted signal receiver 118 (e.g., comprising a coil element) and is interconnected to a microphone assembly 130 via a signal cable 124. The implant housing 100 may be utilized to house a number of components of the implantable hearing instrument. For instance, the implant housing 100 may house an energy storage device and a signal processor. Various additional processing logic and/or circuitry components may also be included in the implant housing 100 as a matter of design choice. In the present arrangement, the signal processor within the implant housing 100 is electrically interconnected to a transducer 108. In the present embodiment, the transducer 108 is connected to the implant housing via first and second signal cables 106, 107. These signal cables 106, 107 are connected by a detachable connector 80.

As illustrated in FIG. 2, the transducer 108 is supportably connected to a positioning system 110, which in turn, is connected to a bone anchor 116 mounted within the patient's mastoid process (e.g., via a hole drilled through the skull). The transducer 108 includes a connection apparatus 112 for connecting the transducer 108 to the ossicles 120 of the patient. In a connected state, the connection apparatus 112 provides a communication path for acoustic stimulation of the ossicles 120, e.g., through transmission of vibrations to the incus 122.

Referring to FIGS. 1 and 3, it is noted that microphone assembly 130 in the present embodiment is a pendant microphone that is connected to the implant housing via a signal cable 124. Use of such a pendant microphone allows the microphone assembly 130 to be spaced from the implant housing 100 such that it need not be mounted to the skull of a patient. Such spacing may facilitate vibration attenuation as well as reduce the number of components that need to be mounted in/on the limited space on the skull near the patient's ear (e.g., mounted near the mastoid process). However, it will be appreciated that in other embodiments, the microphone may be mounted or integrally formed on or within the implant housing 100.

The microphone assembly 130 includes a housing 134 and diaphragm 132 that is positioned to receive ambient acoustic signals through overlying tissue. During normal operation, acoustic signals are received subcutaneously at the diaphragm 132 of the microphone assembly 130. Internal components of the microphone assembly 130 generate an output signal that is indicative of the received acoustic signals. The output signal is provided to the implant housing 100 via the signal cable 124. Upon receipt of the output signal, a signal processor within the implant housing 100 processes the signals to provide a processed audio drive signal, via the connected signal cable 106 and 107, to the transducer 108. As will be appreciated, the signal processor may utilize digital processing techniques to provide frequency shaping, amplification, compression, noise reduction and/or other signal conditioning, including conditioning based on patient-specific fitting parameters. The audio drive signal causes the transducer 108 to transmit vibrations at acoustic frequencies to the connection apparatus 112 to effect the desired sound sensation via mechanical stimulation of the incus 122 of the patient. Similar processes may be utilized for cochlear stimulation devices.

An external charger (not shown) may be utilized to transcutaneously re-charge the energy storage device within the implant housing 100. Such an external charger may include a power source and a transmitter that is operative to transcutaneously transmit, for example, RF signals to the implanted receiver 118. In this regard, the implanted receiver 118 may also include, for example, rectifying circuitry to convert a received signal into an electrical signal for use in charging the energy storage device. The external transmitter and implanted receiver 118 may each comprise coils for inductive coupling of signals there between. In addition to being inductively coupled with the implanted receiver 118 for charging purposes, such an external charger may also provide program instructions to the processor(s) of the implantable hearing instrument.

Combined Signals

Figure 4:
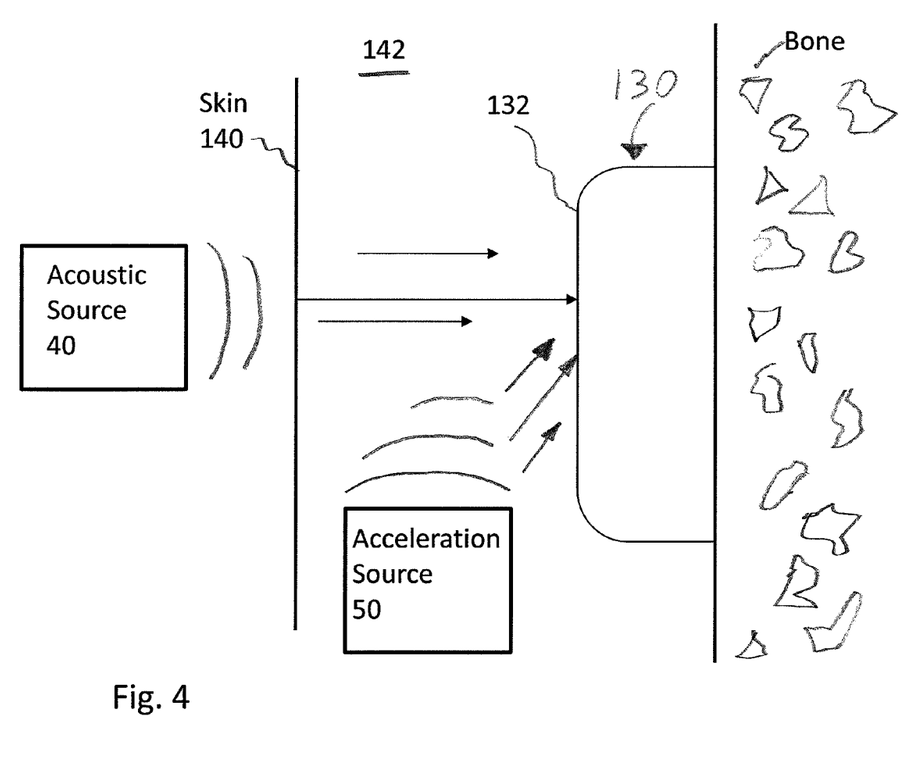
FIG. 4 illustrates the combination of acoustic-induced vibration and acceleration-induced vibration by a microphone diaphragm.

FIG. 4 illustrates how pressures resulting from ambient acoustic sounds and tissue-borne acceleration are combined at an implanted microphone diaphragm 132 of an implantable microphone assembly 130. As shown, the implanted microphone diaphragm 132 is exposed to pressure in overlying tissue 142 that is generated externally to the patient as represented by ambient sound source 40. This ambient acoustic signal (e.g., sound) from the sound source 40 passes through and is filtered by the tissue 142 overlying the microphone diaphragm 132. The deflection of the microphone diaphragm 132 by the pressure associated with the ambient sound results in a desired signal component, or, microphone acoustic response. This microphone acoustic response is also mixed with the pressure generated by vibrations in the overlying tissue 142 caused by one or more acceleration sources 50. The pressure from the acceleration source 50 is likewise filtered by the tissue 142 overlying the microphone diaphragm 132 and results in an undesired signal component or microphone vibration response.

The acceleration source 50 may comprise any source of tissue-borne vibrations and may include biological sources and mechanical sources. Such biological sources may include, without limitation, chewing and speaking. One example of a mechanical source includes feedback signals from the transducer 108, which in the normal course of its operation may vibrate surrounding tissue. Such vibration may subsequently be conducted to the location of the microphone diaphragm 132.

The net effect is that the pressure variations associated with the acoustic source 40 and acceleration source 50 are summed by the normal action of the microphone diaphragm 132. That is, pressure associated with each of the ambient acoustic source and acceleration source, which arrive at the microphone diaphragm 132 through the overlying tissue 142, deflect the diaphragm 132 and generate a combined microphone response or output signal. That is, such an output signal is a combination of the pressure associated with the two sources 40, 50.

As the microphone diaphragm 132 detects the combination of the pressure fluctuations as a single varying pressure, it is desirable for the implanted microphone to compensate for undesired signal components (e.g., the microphone vibration response) in order to detect desired signal components (e.g., the microphone acoustic response) with sufficient sensitivity. Stated otherwise, it is desirable for the microphone assembly 130 to separate ambient acoustic signals from tissue-borne vibration-induced signals.

A number of previous systems have attempted to separately measure the motion acting on the implant housing and subsequently subtract this motion (e.g., acceleration acting on the implant housing) from the combined microphone response. In such systems, one element of the microphone assembly 130 is designed to be preferentially sensitive to acceleration-induced vibration and preferentially insensitive to acoustic stimulation. Such microphones typically include a motion sensor that is disposed within the microphone housing such that it is primarily sensitive to acceleration (i.e., non-ambient vibration acting on the housing) while being substantially insensitive to ambient acoustic signals acting on the microphone diaphragm. In this regard, an output response of the motion sensor may be removed from a combined output response of the microphone diaphragm 132. That is, the output of the motion sensor may be used to estimate and cancel/subtract signals originating from an acceleration source from the combined microphone response. The remaining signal, which is more representative of the ambient acoustic signal, is used by the implanted signal processor 104 to generate a drive signal for use by a transducer to stimulate a component of a patient's auditory system.

Previous systems that have separately measured the responses of a microphone diaphragm and a motion sensor include co-assigned U.S. Pat. Nos. 7,214,179; 7,522,738; 7,556,597 and 7,775,964, the entire contents of each of which is incorporated herein by reference. These patents provide various systems where an output of a motion sensor is measured, scaled, and subtracted from a combined output response of a microphone element. That is, the microphone element generates an electrical output signal from which an electrical motion sensor output signal is subtracted. The necessary scaling and subtraction of the motion sensor signal can result in the addition of electrical noise to the system, which limits the achievable gain of the hearing system. Accordingly, it would be desirable to reduce the magnitude of the motion/acceleration response in the microphone output to reduce subsequent processing requirements and/or allow for improving overall gain of the hearing system.

Optical Measurement

Aspects of the presented inventions are based in part on the recognition that an acoustic response of a microphone diaphragm may be at least partially isolated from a vibration response during measurement using an optical measurement system that measures relative movement between a microphone diaphragm and a moveable cancellation element such as a proof mass. Such a system may reduce or eliminate the need for subsequent processing to compensate for undesired signal components.

Figure 5:
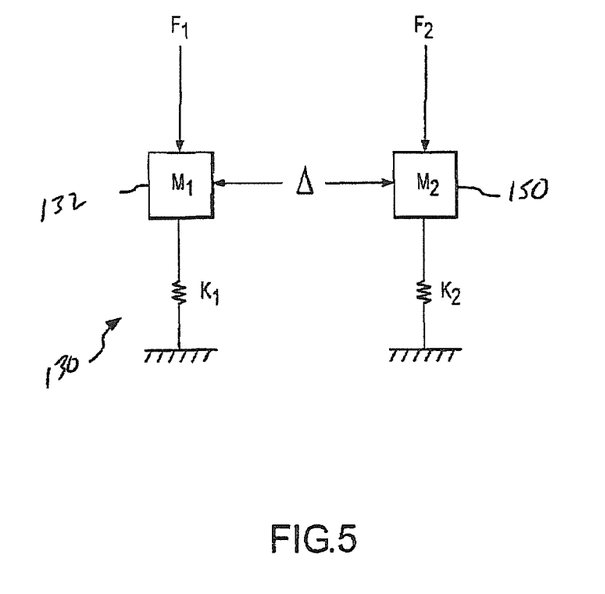
FIG. 5 illustrates a mathematical depiction of the response of a microphone and cancellation element to applied acoustic and acceleration forces.

FIG. 5 shows a schematic/mathematical depiction of the basic operating principle of a microphone assembly 130 that allows for isolating the acoustic response of a microphone diaphragm output by determining the relative movement between the microphone diaphragm and a movable cancellation element 150. The cancellation element is typically a seismic or proof mass that acts as a damped mass on a spring or other compliant support.

As shown, the microphone assembly 130 can be modeled as a spring mass system where the diaphragm 132 and a mass of overlying tissue is a first mass $M_1$ having a first spring constant $k_1$. The diaphragm 132 may be positioned immediately adjacent and facing to the skin of the patient such that a combined force $F_1$, including ambient acoustic induced pressures and acceleration induced pressures, acts upon $M_1$. The cancellation element 150 is substantially isolated from ambient acoustic signals (e.g., within an implant housing). The cancellation element is represented by $M_2$, has a second spring constant $k_2$, and is acted upon by $F_2$, which is the force due to acceleration and substantially free of acoustic forces.

The response of the two systems $M_1$ and $M_2$ is governed by simple harmonics. It can be shown mathematically that when the microphone assembly 130 measures a frequency significantly higher that the resonant frequencies of the systems $M_1$, $k_1$ and $M_2$, $k_2$, the difference in movement $\Delta$ (i.e., relative movement) between the systems may be determined and is independent of spring rates and masses of the systems. Further, the difference in movement $\Delta$ between the cancellation element 150 and the diaphragm 132 is caused by the differences in the forces applied to these elements and specifically by the ambient acoustic forces applied to the diaphragm. That is, the relative movement $\Delta$ represents the ambient acoustic forces applied to the diaphragm 132 substantially free of acceleration forces. In this regard, by measuring the relative movement $\Delta$ between the systems $M_1$ and $M_2$ the acoustic signal may be determined free of or with a reduced response to acceleration induced forces.

The present disclosure improves upon existing systems that separately measure microphone output and motion sensor signals by employing optical measuring to directly measure the relative movement between a microphone diaphragm and a cancellation element. Generally, the presented systems and methods identify a change in a distance or path length between an inside surface of a diaphragm that hermetically covers an aperture in an implantable housing and a cancellation element that is compliantly mounted within the implantable housing.

In the case of an implanted microphone, if the diaphragm and cancellation element move in near unison in response to common acceleration forces, differences in the distance or path length between these elements (i.e., relative movement) will substantially correspond to the acoustic forces acting on the microphone diaphragm. Therefore, to accurately measure the change in the path length and hence isolate the acoustic response, it is desirable that the diaphragm and cancellation element react similarly to acceleration forces. That is, it may be desirable that the magnitude of the cancellation element response to acceleration substantially match the response of the diaphragm to acceleration. Likewise, the phases should be substantially matched as well in order to achieve enhanced acoustic isolation. It may be preferred that such magnitude and phase matching occur in a frequency range of interest (e.g., an acoustic hearing range). This may require that the resonant frequency of each the diaphragm and cancellation element be less than about 2000 Hz and more preferably less than about 200 Hz. These resonant frequencies are typically below an acoustic hearing frequency range. Further, it may be desirable that the diaphragm and cancellation element have substantially equal resonant frequencies and/or equal damping factors. As will be appreciated, with appropriate choice of spring rates for the diaphragm and cancellation element suspension, it is possible to match the response of the diaphragm and cancellation element and thereby make the change in a path length between these elements less sensitive to acceleration induced vibration (e.g., produce near unitary movement), while preserving sensitivity to acoustic pressures acting on the diaphragm. The resulting system may have fewer components, may be manufactured more compactly and inexpensively and offer signal-to-noise ratio improvement in comparison to systems that measure a combined response of a microphone and subsequently cancel a motion signal from the combined response.

Figure 6A:
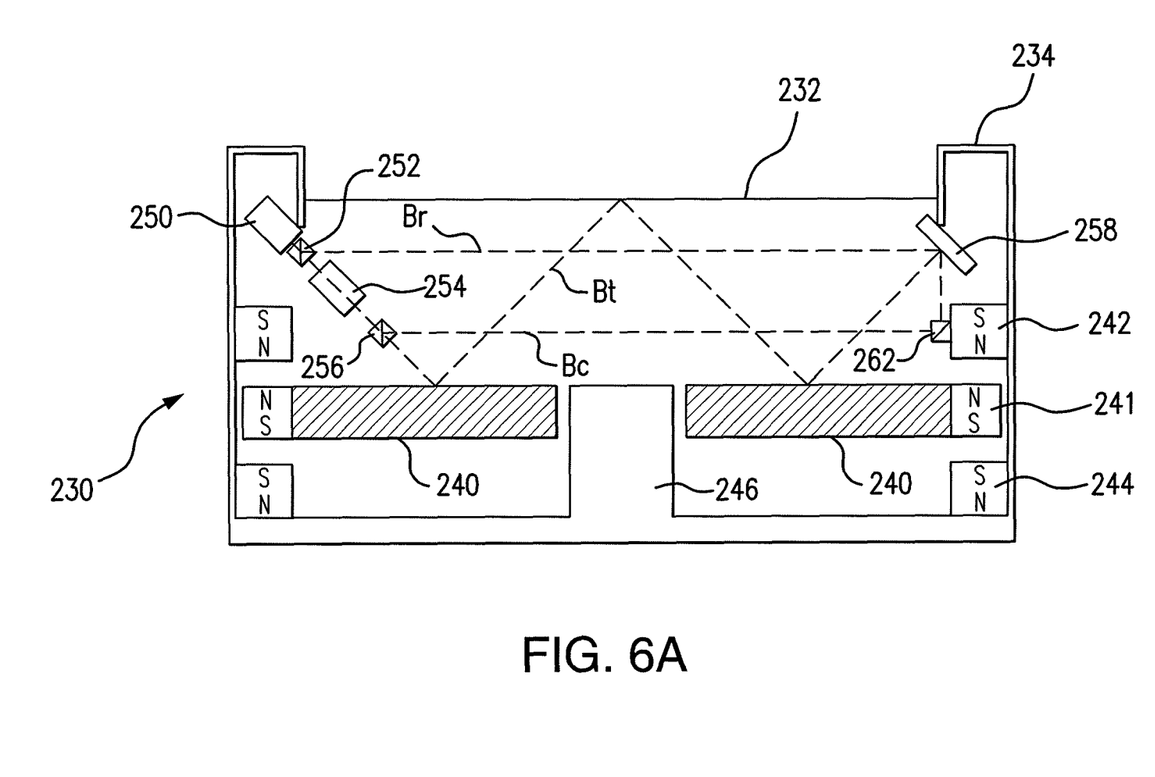
FIG. 6A illustrates a cross-sectional side view of one embodiment of a microphone that allows optically isolating an acoustic response of the microphone diaphragm.
Figure 6B:
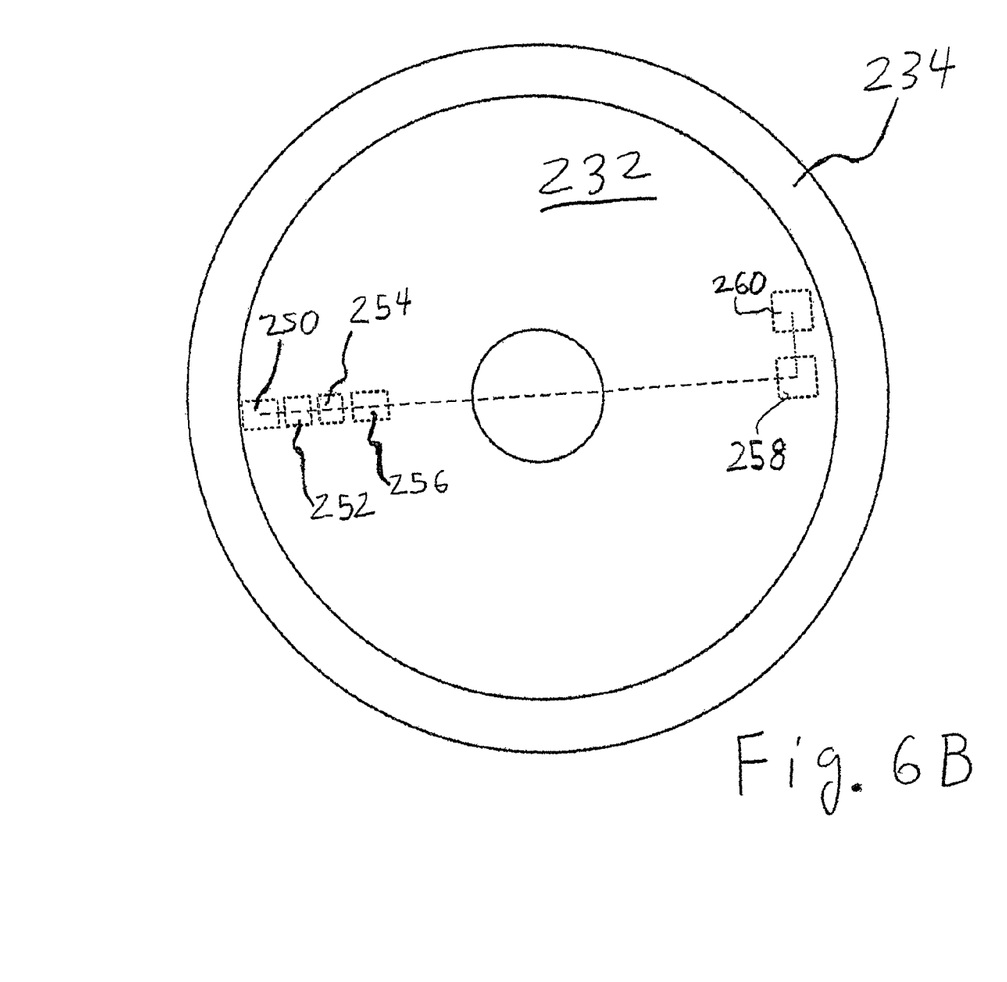
FIG. 6B illustrates a top view of the microphone of FIG. 6A.

FIGS. 6A and 6B illustrate one embodiment of a microphone assembly 230 that allows for optically isolating an acoustic response of a microphone diaphragm. As shown, the microphone assembly 230 includes a microphone diaphragm 232, which is responsive to acoustic signals and vibration induced acceleration, and a compliantly supported proof mass 240, which is primarily responsive to vibration induced acceleration. The microphone diaphragm 232 serves as a hermetic seal for the microphone housing 234 and thereby, upon implant, isolates an internal chamber of the microphone assembly 230 from the user's body. The proof mass 240 is a motion sensitive element that is suspended compliantly within the housing to move relatively to the housing in response to acceleration acting on the housing. The suspension can be (for example) a set of coil, leaf, or pneumatic springs. In the embodiment shown, the proof mass is mounted within a ring magnet 241 polarized along its axis of symmetry and suspended between two fixed ring magnets 242 and 244 polarized so as to maintain the proof mass 240 statically between them. Magnetic suspension, as shown here, has the advantage that the spring rate is small near the center of excursion, permitting relatively large movements in response to vibration. The proof mass 240 may be guided, as shown here, by a post 246 extending through a hole in its center.

Generally, the displacement/movement of the microphone diaphragm 232 and the proof mass 240 are designed to be substantially equal in response to acceleration forces. In contrast, displacement of the diaphragm 232 due to acoustic forces, which do not act on the proof mass, will result in relative movement between the diaphragm 232 and the proof mass 240 and thereby change a path length there between.

In the present embodiment, the relative movement between the microphone diaphragm 232 and the proof mass 240 is measured using an output beam from a laser source 250. More specifically, the output beam travels a path between the laser source 250 and a photo detector 260 where the path includes at least one reflection off the diaphragm 232 and at least one reflection off of the proof mass 240. In this regard, non-unitary movement (e.g., relative movement)

between the diaphragm 232 and proof mass 240 alters the path length between the laser source 250 and the photo detector 260. This change in the path length induces frequency and amplitude shifts (e.g., Doppler shifts) in the output beam. That is, the movement of the diaphragm relative to the cancellation element, which may correspond primarily to ambient acoustic forces acting on the diaphragm 232, modulates the output beam. Demodulating an output signal of the photo detector provides a signal that is indicative of the vibration of the microphone diaphragm 232 in response to ambient acoustic signals (e.g., sound) with a reduced response to acceleration induced-vibration. Stated otherwise, the output beam from the laser source allows for more directly measuring relative movement Δ between the diaphragm 232 and the proof mass 240 and generating an acoustic response output signal that may be utilized for hearing augmentation purposes.

The embodiment of FIGS. 6A and 6B utilizes a laser Doppler velocimeter (LDV) configuration for measurement. In this configuration, the laser source directs a first beam at the surfaces of interest or vibrating targets (e.g., diaphragm and proof mass), such that relative vibration amplitude and frequency are extracted from the Doppler shift of the laser beam frequency due to the relative motion of these vibrating surfaces. The LDV is generally a laser interferometer that employs two or more laser beams to measure the frequency (or phase) difference between a reference beam and a test beam. The test beam is directed to the target, and scattered light from the target is collected and interfered with the reference beam on a photodetector, typically a photodiode. Most vibrometers also add a known frequency shift (typically 30-40 MHz) to one of the beams. This frequency shift may be generated by a Bragg cell or other acousto-optic modulator. The output of an LDV is generally a continuous analog voltage that is directly proportional to the target velocity component along a direction of the laser beam.

Light from the target is reflected to the photo detector where it is combined with the reference beam. The initial frequency of the laser is typically very high ($>10^{14}$ Hz), which is higher than the response of the detector. The detector does respond, however, to the beat frequency between the beams. The output of the photodetector is a frequency modulated (FM) signal, with the Bragg cell frequency as the carrier frequency, and the Doppler shift as the modulation frequency. This signal can be demodulated to derive the velocity vs. time of the vibrating target. By comparing the shift in the laser beam to a reference laser beam (i.e., without a Doppler shift) the vibration profile/signature of the surface may be determined. Thus, by reflecting the laser beam off of both the microphone diaphragm and the proof mass it is possible to directly measure the relative movement between these elements which, as discussed above, corresponds to the acoustic forces impinging on the diaphragm. In this regard, the acoustic response can be isolated from a combined output using a single sensing device.

Referring again to FIGS. 6A and 6B, it is noted that in the present embodiment, the laser source 250 (for example, a diode laser) emits a beam passing through in sequence, a first beam splitter 252, a Bragg cell 254, and a second beam splitter 256. Thus, the present embodiment splits the initial output beam into three beams ($B_r$, $B_c$ and $B_t$). Specifically, the first beam splitter 252 splits the initial output beam of the laser source into two beams having identical characteristics (e.g. frequency, amplitude, etc.). One of those beams is designated the reference beam $B_r$ and is provided to the photodiode 260 free of reflection off of the vibrating surfaces 232, 240. The other output of the first beam splitter travels through the second beam splitter 256 forming two beams: a comparison beam $B_c$ and test beam $B_t$. The comparison beam $B_c$ and test beam $B_t$ are both shifted in frequency by the Bragg Cell. In the present embodiment, the reference beam Br travels a path to the photodiode 260 via a mirror 258 and a third beam splitter 262. Upon exiting the second beam splitter 256, a comparison beam $B_c$ is also transmitted to the third beam splitter 262 for provision to the photodiode 260. The two beams $B_c$ and $B_r$ are combined at the third beam splitter 262 and directed to the photo detector 260.

The test beam $B_t$, after exiting the second beam splitter 256 travels an optical path that reflects off of both the proof mass 240 and an inner surface of the diaphragm 232 to a mirror 258, which directs the beam to the photodiode 260 via the third beam splitter 262. To permit such a travel path, the inside surface of the diaphragm and at least one surface of the proof mass have reflective surfaces. In this regard, such surfaces may be polished to achieve a desired reflectance or these surfaces may incorporate a reflective coating.

The Bragg cell 254 introduces a frequency shift to the test beam and comparison beam, causing the combined beams $B_c$ and $B_r$ to interfere at a beat frequency equal to the Bragg cell shift. Non-unitary movement of the diaphragm 232 and proof mass 240 alters the path length of the test beam $B_t$ and thereby introduce a Doppler shift to the beam. The photo detector 260 receives the beat frequency modulated by the Doppler shift determined by the apparent velocity, or change in path length, with time of the test beam $B_t$. As noted, the photo detector generates a frequency modulated signal that may be demodulated to yield a signal corresponding to the apparent velocity along $B_t$. This apparent velocity is the acoustic response of the microphone diaphragm.

Figure 7:
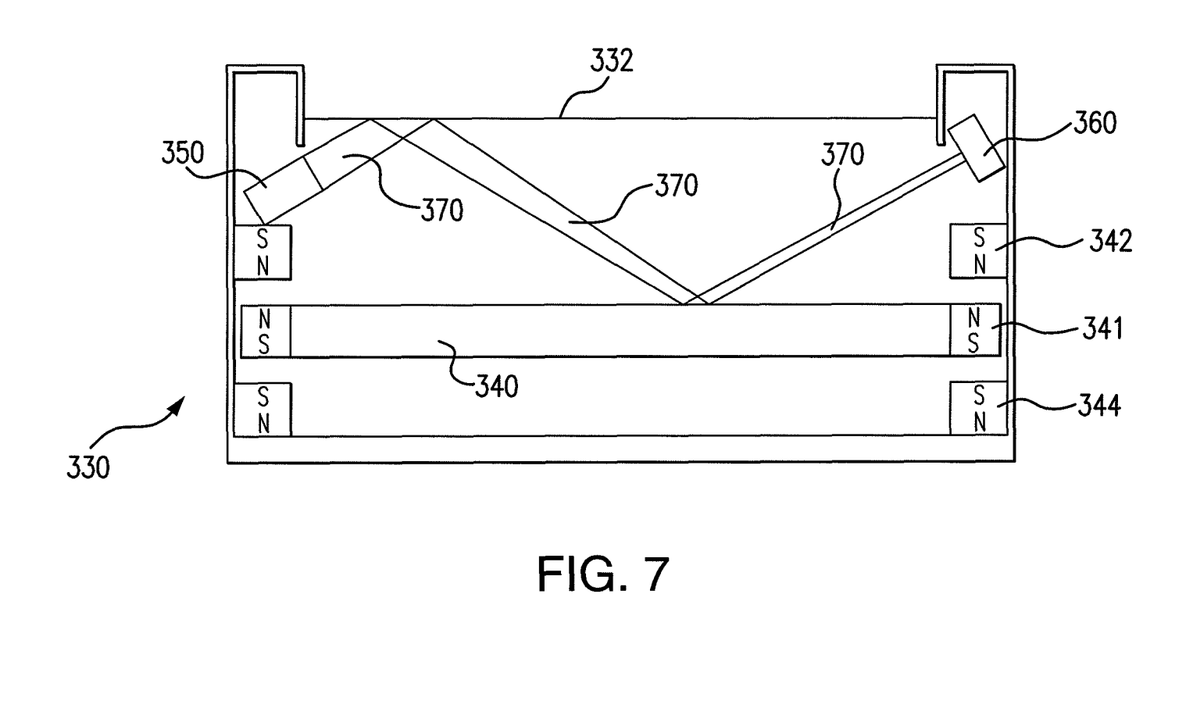
FIG. 7 illustrates a cross-sectional side view of another embodiment of a microphone that allows optically isolating an acoustic response of the microphone diaphragm.

FIG. 7 illustrates another embodiment of a microphone assembly 330 that allows for isolating an acoustic response of a microphone diaphragm. Similar to the embodiment of FIG. 6A the microphone assembly 330 includes a microphone diaphragm 332, which is responsive to acoustic signals and vibration induced acceleration, and a compliantly supported proof mass 340, which is primarily responsive to vibration induced acceleration. The proof mass 340 is a motion sensitive element that is mounted within a ring magnet 341 polarized along its axis of symmetry and suspended between two fixed ring magnets 342 and 344 polarized so as to maintain the proof mass 340 statically between them. Other arrangements may utilize other compliant supports such as coil, leaf, or pneumatic springs.

As above, the displacement/movement of the microphone diaphragm 332 and the proof mass 340 are designed to be substantially equal in response acceleration forces and differ in response to acoustic forces. That is, acoustic forces act primarily on the diaphragm 332 and result in relative movement between the diaphragm 332 and the proof mass 340 and thereby change a distance or path length there between.

The relative movement between the microphone diaphragm 332 and the proof mass 340 is measured using an output beam from a laser source 350. More specifically, the output beam travels a path between the laser source 350 and a photo detector 360 where the path includes at least one reflection off the diaphragm 332 and at least one reflection off of the proof mass 340. In this regard, non-unitary movement (e.g., relative movement) between the diaphragm 332 and proof mass 340 alters the path length between the laser source 350 and the photo detector 360.

Figure 8:
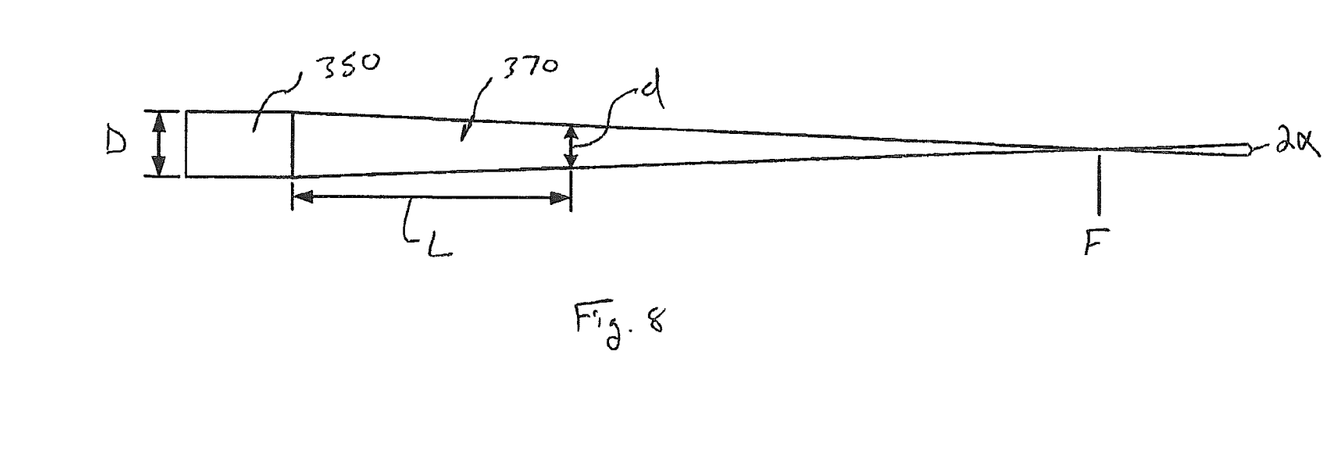
FIG. 8 illustrates an operating principle of the microphone of FIG. 7.

In the present embodiment, the change in the path length is measured by monitoring the change in a diameter of a convergent laser beam as measured at a receiving photo detector 360. In such a convergent laser beam, the output beam may be a conical beam that converges at a focal point a known length from the laser source. FIG. 8 illustrates such a converging beam. As shown, the beam 370 emits from a laser source 350 having an initial diameter D. Further, the beam 370 converges at a constant angle α until it converges at focal point F. After passing thought the focal point F the laser beam 370 diverges. Importantly, the diameter d of the beam at any length L measured from the source 350 can be calculated:

$$d = D - L\alpha \qquad \text{eq. 1}$$

The ability to calculate the diameter at any location along the beam also permits calculating a change in a path length by monitoring a change in the diameter d of the beam at a fixed location.

Referring again to FIG. 7, it is noted that the output beam 370 of the laser source 350 reflects off of the diaphragm 332, proof mass 340 and is received by a photo detector 360. When the system is static (i.e., diaphragm 332 and proof mass are not moving), the photo detector 360 receives the beam 370 having fixed diameter $d_1$, and generates an output indicative of this beam diameter. When the diaphragm and proof mass move in unison, the path length between the source 350 and photo detector 360 is unchanged and the diameter of the received beam remains unchanged (e.g., $d_1$), though the position of the beam on the photo detector may change. In contrast, when there is relative movement between the diaphragm 332 and proof mass 340 due to acoustic forces acting on the diaphragm 332, the path length between these elements changes. The change in path length changes the diameter of the beam received by the photo detector 360 (e.g., $d_2$). Likewise, the output of the photo detector also changes. Accordingly, as the initial diameter D and convergence angle α are known and fixed, knowledge of the change of diameter at the photo detector allows for calculating the change of the path length as a function of time. Based on known geometric relationships (e.g., beam reflectance angles, static path length, etc.) the displacement of the diaphragm to the proof mass (e.g., relative movement) can be derived. Again, this displacement is indicative of the acoustic forces acting on the diaphragm having a reduced response to acceleration induced vibration in overlying tissue.

In either of the above-noted embodiments, the isolated output signal of the microphone may be utilized to generate a drive signal for operating a transducer of an implantable hearing instrument. In some instances, the isolated signal may be utilized with minimal additional processing. However, in other arrangements, additional processing may be performed. Such additional processing may include subtraction/cancellation of a measured motion signal to further reduce the motion response in the output signal of the microphone. In such arrangements, it will be appreciated that the motion of the proof mass may be monitored to generate such a motion signal. Additionally or alternatively, signals from other motion sensing elements may be utilized.

Those skilled in the art will appreciate variations of the above-described embodiments that fall within the scope of the invention. For instance, it may be advantageous to mount a laser source or detector to a cancellation surface. In such an arrangement, the source or detector may move in response to acceleration acting on the housing. Such an arrangement may simplify beam reflectance and/or minimize the number of reflections between the source and detector. However, it will also be appreciated that additional reflections between the diaphragm and cancellation surface may allow for increasing the sensitivity of the system. In this regard, it may be desirable to increase the number of reflections off of each surface. As a result, the invention is not limited to the specific examples and illustrations discussed above, but only by the following claims and their equivalents.

The invention claimed is:

1. A method, comprising:
   exposing a first surface to a first light beam while the first surface moves due to energy resulting from at least sound;
   exposing a second surface to the first light beam while the second surface moves due to a second energy different from the at least sound;
   detecting at least a portion of the first light beam after the first light beam has reflected off of the first surface and off of the second surface while the first and second surfaces are moving due to the respective energies.

2. The method of claim 1, wherein the first surface is moving in response to one of acoustic forces or a combination of acoustic and acceleration forces and wherein said second surface is moving in response to said acceleration forces.

3. The method of claim 1, wherein the first and second surfaces are part of a microphone.

4. The method of claim 1, wherein said first and second surfaces are moving substantially in unison in relation to acceleration forces acting on at least a part of a microphone including the first and second surfaces.

5. The method of claim 1, further comprising:
   detecting a reference beam that has not interacted with at least one of the first or second surfaces.

6. The method of claim 1, wherein:
   the detected light has travelled along a path having a distance that is varying due to the movement of both the first and second surfaces.

7. The method of claim 6, further comprising:
   splitting an output beam of a light source to generate said first light beam and a second light beam, wherein said first and second light beams initially have common characteristics.

8. The method of claim 1, wherein:
   the first surface is an inside surface of an assembly of an implantable hearing instrument implanted in a recipient;
   the second surface is part of a cancellation element compliantly disposed within the assembly; and
   the method further comprises receiving said first light beam at an optical detector after reflection off of the first surface and the second surface, wherein said optical detector generates an output signal indicative of relative movement between the first surface and the second surface.

9. The method of claim 8, wherein:
   the first surface and the second surface are moving substantially in unison in relation to acceleration forces acting on the assembly.

10. The method of claim 8, further comprising:
    processing said output signal; and
    generating a vibration signature based on the processing of the output signal, the vibration signature being a vibration signature of the inside surface of the housing.

11. The method of claim 10, further comprising:
    generating a stimulation signal using the vibration signature; and
    evoking a hearing percept using an implanted actuator based on the stimulation signal.

12. The method of claim 7, further comprising:
shifting a frequency of said first light beam a predetermined amount.

13. The method of claim 12, further comprising generating an output signal indicative of modulation to the first light beam in accordance with vibration of said first surface in response to acoustic forces acting on an outside surface of at least a portion of a microphone.

14. The method of claim 1, further comprising:
exposing the first surface to a second light beam while the first surface moves due to energy resulting from only acceleration forces;
exposing the second surface to the second light beam while the second surface moves due to only the acceleration forces;
detecting at least a portion of the second light beam after the second light beam has reflected off of the first surface and off of the second surface while the first and second surfaces are moving due to the acceleration forces.

15. The method of claim 14, wherein said first and second surfaces are moving substantially in unison in relation to acceleration forces.

16. A method, comprising:
directing light along an optical path including a length between a first reflective surface that is vibrating in response to energy at least in part resulting from sound and a second reflective surface that is moving in response to energy at least less in part resulting from sound than the part of the energy to which the vibration of first reflective surface results, the first and second reflective surfaces being reflectively optically aligned with one another;
generating an output signal indicative of a change in said length over time; and
processing said output signal to obtain data indicative of the vibration of the first surface.

17. The method of claim 16, further comprising measuring said path length by reflecting a first laser beam off of said first reflective surface and said second reflective surface to generate a modulated beam, wherein processing comprises demodulating said modulated beam.

18. The method of claim 16, further comprising measuring said path length by reflecting a first laser beam off of said first reflective surface and said second reflective surface and generating an output signal indicative of a diameter of said first laser beam after reflecting.

19. The method of claim 16, wherein the first surface is a diaphragm of an implanted microphone implanted in the recipient, and the vibration of the first surface is an acoustic response of the diaphragm.

20. A method used in an implanted hearing instrument, comprising:
reflecting a first light beam off of an inside surface of a housing of said implantable hearing instrument;
reflecting said first light beam off of a cancellation element compliantly disposed within an internal chamber of said housing; and
receiving said first light beam at an optical detector after reflection off of said inside surface of said housing and said cancellation element, wherein said optical detector generates an output signal indicative of relative movement between said inside surface and said cancellation element, wherein the output signal is indicative of at least substantially only ambient sound to the extent that ambient sound is present.

21. The method of claim 20, wherein said inside surface of said housing moves in response to any one of acoustic forces, acceleration forces or a combination of said acoustic and acceleration forces and wherein said cancellation element moves in response to said acceleration forces.

22. The method of claim 21, wherein said inside surface and said cancellation element move substantially in unison in relation to acceleration forces acting on said housing.

23. The method of claim 20, further comprising:
processing said output signal to generate a vibration signature of the inside surface of said housing.

24. The method of claim 23, further comprising:
generating a stimulation signal using said vibration signature, said stimulation signal being operative for actuating an actuator of an implantable hearing instrument.

25. The method of claim 20, further comprising:
receiving a second light beam at said optical detector, wherein said second light beam is a reference beam.

26. The method of claim 25, further comprising:
splitting an output beam of a light source to generate said first and second light beams, wherein said light beams initially have common characteristics.

27. The method of claim 26, further comprising:
shifting a frequency of said first beam a predetermined amount at a location between the light source and said optical detector.

* * * * *